(12) United States Patent
Garcia-Contreras et al.

(10) Patent No.: US 11,534,397 B2
(45) Date of Patent: Dec. 27, 2022

(54) NANOCRYSTAL MICROPARTICLES OF POORLY SOLUBLE DRUGS AND METHODS OF PRODUCTION AND USE THEREOF

(71) Applicant: The Board of Regents of the University of Oklahoma, Norman, OK (US)

(72) Inventors: Lucila Garcia-Contreras, Edmond, OK (US); Sevim Manolya Hatipoglu, Oklahoma City, OK (US); Doris Manglaracina Benbrook, Oklahoma City, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 17/171,151

(22) Filed: Feb. 9, 2021

(65) Prior Publication Data
US 2021/0161812 A1    Jun. 3, 2021

Related U.S. Application Data

(63) Continuation-in-part of application No. 16/183,368, filed on Nov. 7, 2018, now abandoned.

(60) Provisional application No. 62/583,755, filed on Nov. 9, 2017.

(51) Int. Cl.
*A61K 9/00*    (2006.01)
*A61K 9/50*    (2006.01)
*A61K 31/382*    (2006.01)

(52) U.S. Cl.
CPC .......... *A61K 9/0075* (2013.01); *A61K 9/5015* (2013.01); *A61K 9/5089* (2013.01); *A61K 31/382* (2013.01)

(58) Field of Classification Search
CPC .. A61K 9/1694; A61K 9/0075; A61K 9/1623; A61K 9/1682; A61K 31/382
See application file for complete search history.

(56) References Cited

U.S. PATENT DOCUMENTS

| | | |
|---|---|---|
| 6,586,460 B1 | 7/2003 | Berlin et al. |
| 7,612,107 B2 | 11/2009 | Benbrook et al. |
| 2002/0102294 A1* | 8/2002 | Bosch .................... A61K 9/008 424/450 |
| 2004/0156859 A1* | 8/2004 | Ezrin ........................ A61P 9/06 424/185.1 |
| 2010/0260858 A1* | 10/2010 | Ruddy ................. A61K 31/436 424/492 |

(Continued)

OTHER PUBLICATIONS

Kabirov et al., ("Oral toxicity and pharmacokinetic studies of SHetA2, a new chemopreventive agent, in rats and dogs", Drug and Chemical Toxicology, 2013; 36(3): 284-295, (Year: 2013).*

(Continued)

*Primary Examiner* — Jianfeng Song
(74) *Attorney, Agent, or Firm* — Dunlap Codding, P.C.

(57) ABSTRACT

Microparticulate drug compositions comprising nanocrystals of poorly soluble drugs combined with a carrier are disclosed. Also disclosed are pharmaceutical compositions that include the microparticulate drug compositions. Further disclosed are methods of preparing and using the microparticulate drug compositions/pharmaceutical compositions.

6 Claims, 9 Drawing Sheets

(56) References Cited

U.S. PATENT DOCUMENTS

2013/0184323 A1* 7/2013 Benbrook ............ A61K 31/38
  514/432

OTHER PUBLICATIONS

Ibrahim et al., "A Novel Tuberculosis Treatment: Inhalable SHetA2 Microparticles for Immediate Release and Macrophage Targeting", Respiratory Drug Delivery, 591-594, Apr. 2016. (Year: 2016).*

American Cancer Society, Cancer Facts & Figures 2016; Atlanta, GA.; American Cancer Society (2016), pp. 1-66.

Benbrook, et al.; "Chemoprevention of Colon and Small Intestinal Tumorigenesis in APC(min/+) Mice by SHetA2 (NSC721689) Without Toxicity," Cancer Prev Res (2013); 6(9):908-916.

Chen, et al.; "Nanonization Strategies for Poorly Water-Soluble Drugs," Drug Discovery Today; (2011); 16 (7/8):354-360.

Garcia-Contreras, et al.; "Dry Powder PA-824 Aerosols for Treatment of Tuberculosis in Guinea Pigs," Antimicrobial Agents and Chemotherapy (2010); 54(4):1436-1442.

Garcia-Contreras, et al.; "Pharmacokinetics of Aerosolized Rifampicin Large Porous Particles in the Guinea Pig," Respiratory Drug Delivery (2006); Healthcare international Publishing, LCC; David River Grove, IL.; pp. 873-876.

Hatipoglu, et al.; "Inhalable Microparticulate SHetA2 Nanocrystals for Lung Cancer Treatment," University of Oklahoma Health Sciences Center Graduate Research Education and Technology (GREAT) Symposium, Oklahoma City, OK. USA, Mar. 2017.

Hatipoglu, et al.; "SHetA2 Nanocrystals as Novel Therapy to Treat Lung Cancer: Formulation and Characterization," AAPS Annual Meeting and Exposition, Denver, CO.; Nov. 13-17, 2016.

Hatipoglu, et al.; "Pharmacokinetics of Inhalable Microparticulate SHetA2 Nanocrystals for Lung Cancer Treatment," AAPS Annual Meeting and Exposition, Nov. 12-15, 2017.

Heyder, et al.; "Deposition of Particles in the Human Respiratory Tract in the Size Range 0.005-15 μm," J. Aerosol Sci., (1986); 17(5): 811-825.

Heyder, et al.; "Mathematical Models of Particle Deposition in the Human Respiratory Tract*," J. Aerosol Sci., (1984), 15(6):697-707.

Ibrahim, et al.; "Optimization of Inhalable ShetA2 Microparticles for Tuberculosis Treatment," AAPS conference, Orlando, FL., Oct. 25-29, 2015.

Ibrahim, et al.; "Dissolution Studies for Inhalable SHetA2 Dry Powder Using Modified Flow through Cell Dissolution Apparatus," AAPS Annual Meeting and Exposition, Denver CO., Nov. 13-17, 2016.

Ige, et al.; "Fabrication of Fenofibrate Nanocrystals by Probe Sonication Method for Enhancement of Dissolution Rate and Oral Bioavailability," Colloids and Surfaces B: Biointerfaces (2013), 108:366-373.

Jinno, et al.; "Effect of Particle Size Reduction on Dissolution and Oral Absorption of a Poorly Water-Soluble Drug, Cilostazol, in Beagle Dogs," Journal of Controlled Release, (2006), 111:56-64.

Kabirov, et al.; "Oral Toxicity and Pharmacokinetic Studies of SHetA2, a New Chemopreventive Agent, in Rats and Dogs," Drug and Chemical Toxicology (2013), 36(3):284-295.

Keck, et al.; "Second Generation of Drug Nanocrystais for Delivery of Poorly Soluble Drugs: SmartCrystals Technology," Dosis (2008) 24:124-128.

Lin, et al.; "CAAT/Enhancer Binding Protein Homologous Protein-Dependent Death Receptors Induction is a Major Component of SHetA2-Induced Apoptosis in Lung Cancer Cells," Cancer Res. (2008), 68(13):5335-5344. Lipinski, et al.; "Experimental and Computational Approaches to Estimate Solubility and Permeability in Drug Discovery and Development Settings," Advanced Drug Delivery Reviews (2001), 46:3-26.

Lipinski, et al.; "Experimental and Computational Approaches to Estimate Solubility and Permeability in Drug Discovery and Development Settings," Advanced Drug Delivery Reviews (2001), 46:3-26.

Naylor, et al.; "Anti-Cancer Activities and Interaction of Imiquimod and Flex-Het, SHetA2, in Melanoma and Ovarian Cancer," Journal of Cancer Therapy (2013), 4:7-19.

Sawant, et al.; "Drug Nanocrystais: Novel Technique for Delivery of Poorly Soluble Drugs," International Journal of Science Innovations and Discoveries (2011), 1(3):1-15.

Sinha, et al.; "Bottom-up Approaches for Preparing Drug Nanocrystais: Formulations and Factors Affecting Particle Size," International Journal of Pharmaceutics (2013),453:126-141.

Wood, et al.; "Aerosolised Antibacterials for the Prevention and Treatment of Hospital-Acquired Pneumonia," Drugs (2007), 67(6):903-914.

Yan Chan, et al.; "A Novel Dry Powder Inhalable Formulation Incorporating Three First-Line Anti-Tubercular Antibiotics," European Journal of Pharmaceutics and Biopharmaceutics (2013), 83:285-292.

Ibrahim, et al; A Novel Tuberculosis Treatment: Inhalable SHetA2 Microparticles for Immediate Release and Macrophage Targeting, Respiratory Drug Delivery (2016) Annual Meeting and Exposition, Scottsdale AZ. , Apr. 17-21, 2016, pp. 591-594.

U.S. Appl. No. 16/183,368, filed Nov. 7, 2018; Office Action dated Feb. 7, 2020.

U.S. Appl. No. 16/183,368, filed Nov. 7, 2018; Amendment and Response to Office Action dated Aug. 7, 2020.

U.S. Appl. No. 16/183,368, filed Nov. 7, 2018; Final Office Action dated Sep. 24, 2020.

* cited by examiner

NANOCRYSTAL MICROPARTICLES OF POORLY SOLUBLE DRUGS AND METHODS OF PRODUCTION AND USE THEREOF

CROSS REFERENCE TO RELATED APPLICATIONS/INCORPORATION BY REFERENCE STATEMENT

This application is a continuation-in-part of U.S. patent application Ser. No. 16/183,368, filed Nov. 7, 2018, which claims benefit under 35 USC § 119(e) of U.S. Provisional Application No. 62/583,755, filed Nov. 9, 2017. The entire contents of the above-referenced patent applications are hereby expressly incorporated herein by reference.

BACKGROUND

One of the main challenges in the treatment of lung diseases such as tuberculosis, cancer, and fungal infections is the poor water solubility of some of the most effective therapeutic compounds to treat these diseases, which causes low oral bioavailability of these therapeutic compounds. As a result, higher doses of these compounds must be used to treat these conditions effectively. However, these high doses can also cause significant adverse effects that decrease the quality of life of patients.

For example, lung cancer is the leading cause of cancer death worldwide and accounts for 26-30% of all cancer deaths in the United States. The two major types of lung cancer are small cell lung cancer (SCLC) and non-small cell lung cancer (NSCLC); NSCLC accounts for 85-90% of lung cancers. From NSCLC, the adenocarcinoma is usually found in the bronchio-alveolar region of the lung. Surgery is the standard of care for stage I NSCLC, whereas for stage II and IIIA adjuvant, cisplatin-based chemotherapy remains the gold standard for completely resected NSCLC tumors. Chemotherapy is usually given systemically (oral or IV), with just a small fraction of the drug reaching the lung, while most is distributed elsewhere in the body. As a result, treatment usually involves administration of high doses, which results in severe side effects and decreased quality of life for the patient.

Cancer chemotherapy is limited by the often poor solubility of drugs and by the toxicity caused by drugs, including (but not limited to) cytotoxic agents which are the most widely used anticancer therapies. To overcome the handicaps of cytotoxic agents, new molecular targeting therapies have been developed. Although they have an improved toxicity profile, administrations of these agents continuously over long time periods causes chronic toxicity, which still remains a key limiting factor.

The number of poorly soluble drugs in use has dramatically increased over the last ten years. Poor solubility in water is associated with low bioavailability. If the drug is not soluble, its absorption will be greatly reduced, and it will not reach the site of action. Efforts have been made to increase the solubility of these poorly soluble compounds. However, the methods which are used to increase the solubility of these poorly soluble drugs are limited due to their chemistry. Some methods include chemical modification or formulation of the compound in a pharmaceutical dosage form. However, chemical modification decreases the effectiveness of some compounds, and traditional dosage forms require the use of excipients that usually increase the amount of material that the patient ingests and may not decrease the required dose.

A common approach to increase the dissolution rate of therapeutic compounds is the reduction of their particle size to micron sizes by milling. Increasing surface area by reducing the size of particles provides a high surface to volume ratio, which effectively increases the dissolution rate by increasing saturation solubility. Yet this size reduction is often not sufficient to increase solubility and drug absorption to therapeutic levels.

As noted, direct pulmonary delivery of poorly soluble compounds in powder formulations can increase their therapeutic efficacy for lung diseases, but this approach is limited by the amount of powder that can be dosed at one time by this route. This approach is further limited when these dry powder formulations contain large amounts of excipients that increase the size of the inhaled dose and that are likely to cause side effects in the respiratory tract and in the lungs. This is the main limitation for the pulmonary delivery of therapeutic agents formulated in nanoparticles, including (but not limited to) polymeric nanoparticles and liposomes. Moreover, pulmonary delivery of nanocrystals by themselves would be difficult, since due to their small size they would simply be exhaled, owing to their low inertia.

It has been hypothesized that nanocrystals (NCs) having sizes below the micron range and consisting of 100% drug may be capable of achieving therapeutic concentration at the site of drug action for these lung diseases with very small powder doses. Nevertheless, dry powder NCs are subject to problems of aggregation due to strong electrostatic forces exhibited by particles of that size, which result in the generation of highly poly-dispersed aerosols consisting of irregular sized particles. Three basic techniques are conventionally used to generate nanocrystals, including milling, precipitation, and homogenization methods.

Elan Nanosystems (San Francisco, Calif.) produces NC products using a proprietary NANOCRYSTAL® technology based on a pearl mill technology. The resulting NC material is used mostly in oral suspensions and tablets. RAPAMUNE® (rapamycin; Pfizer Inc., New York City, N.Y.), for example, is used to avoid organ rejection after a kidney transplantation; it is available in two formulations such as oral suspension and tablet. EMEND® (aprepitant; Merck & Co., Inc., Kenilworth, N.J.) is used to treat emesis; the formulation is prepared by nanonization, and the drug nanocrystals are packed in hard gelatin capsule as pellets.

TRICOR® (fenofibrate) is a drug developed and marketed by Abbott Laboratories (Chicago, Ill.). It is used in tablet form for treatment as adjunctive therapy for hypercholesterolemia or mixed dyslipidemia. MEGACE ES® (megestrol acetate; Par Pharmaceutical Companies, Inc., Spring Valley, N.Y.), is a synthetic progestin known as megestrol which is used to help patients who are suffering from chemotherapy and HIV infection to gain weight. It is formulated as a nanocrystal suspension and administered orally.

However, there is currently no NC powder product which can be used as an aerosol to treat pulmonary diseases by inhalation, for direct delivery of a drug to the lungs. It is to solving this deficiency that the embodiments of the present disclosure are directed.

BRIEF DESCRIPTION OF THE DRAWINGS

FIG. 1 shows SEM images of (a) SHetA2 nanocrystals (NCs) and (b) microparticles (MPs) produced from the SHetA2 NCs.

FIG. 2 shows the size distribution of the respirable fraction of microparticles formed by SHetA2 NCs formulated into microparticles (NC-MPs). The sum of all bars adds to 95%.

Figure 7:
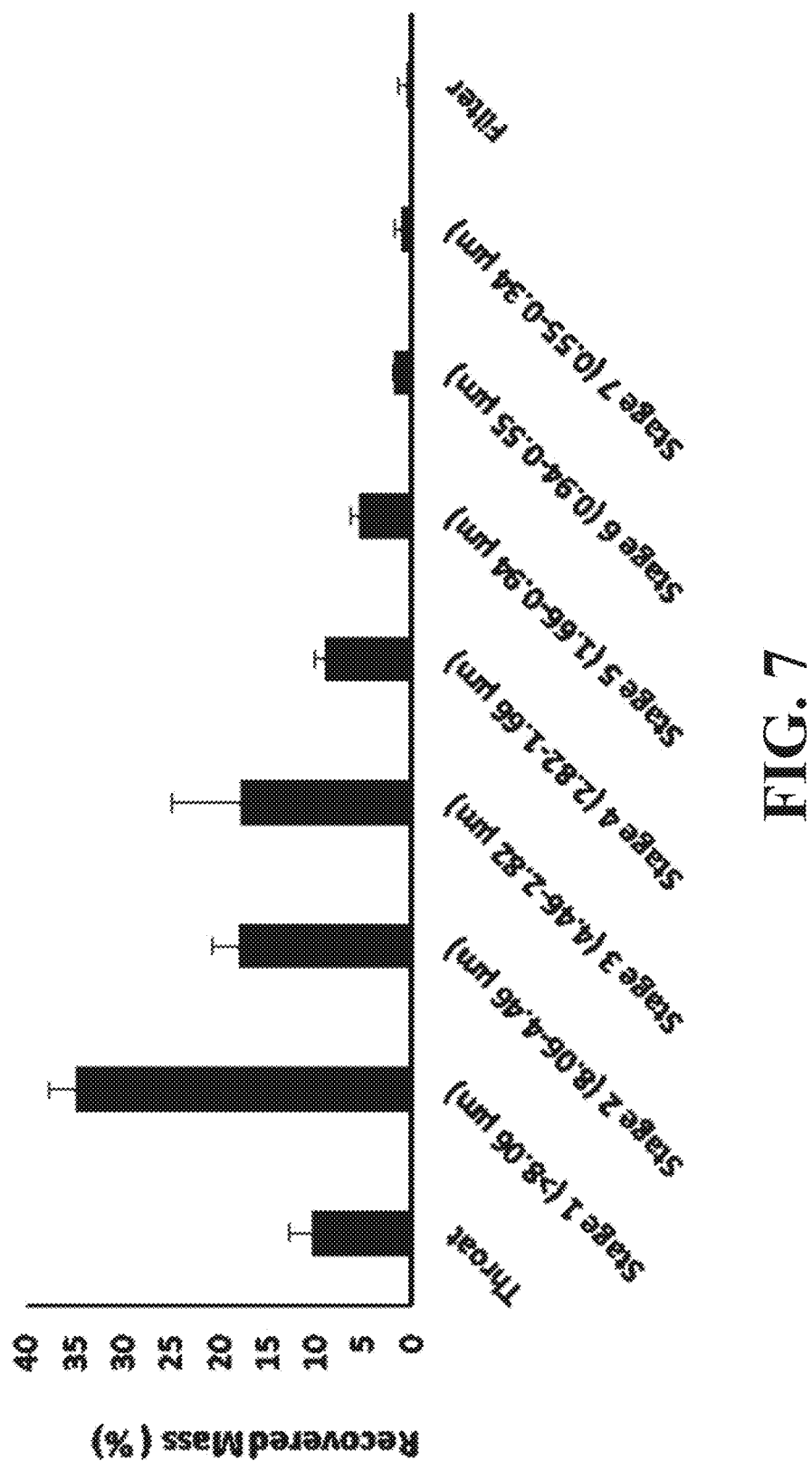

FIG. 7 shows in vitro aerosol performance of SHetA2 NC-MPs. SHetA2 deposition pattern in the collection cups of the Next Generation Impactor (NGI; Copley Scientific, Nottingham, UK) after dispersion of SHetA2 NC-MPs using SPIRIVA® HANDIHALER® (tiotropium bromide inhalation powder; Boehringer Ingelheim Pharmaceuticals, Inc., Ridgefield, Conn.).

Figure 8:
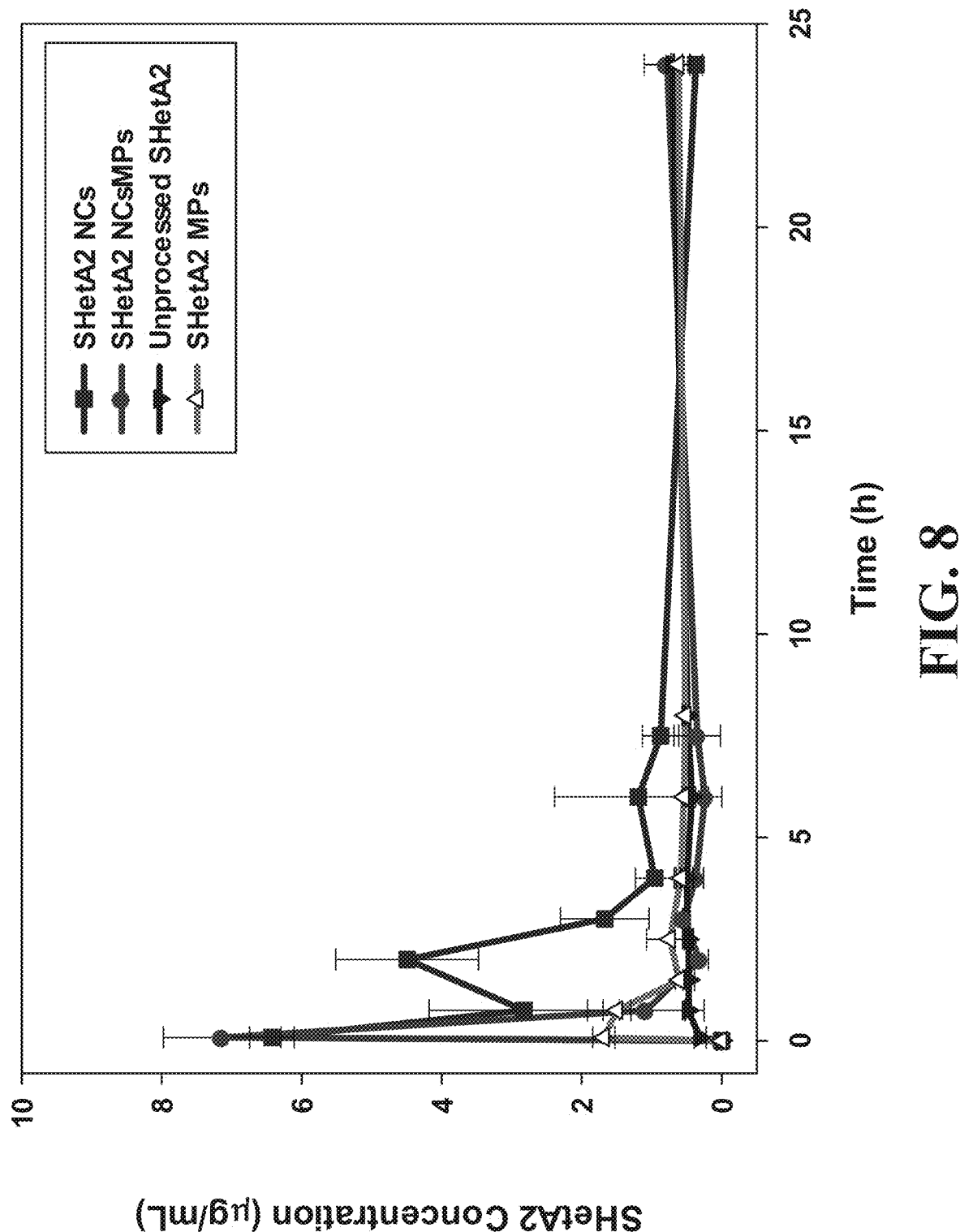

FIG. 8 shows apparent maximum solubilities of SHetA2 NCs and/or MPs from unprocessed SHetA2. SHetA2 NCs, SHetA2 MPs, and SHetA2 NC-MPs in PBS containing 0.05% SDS.

Figure 9:
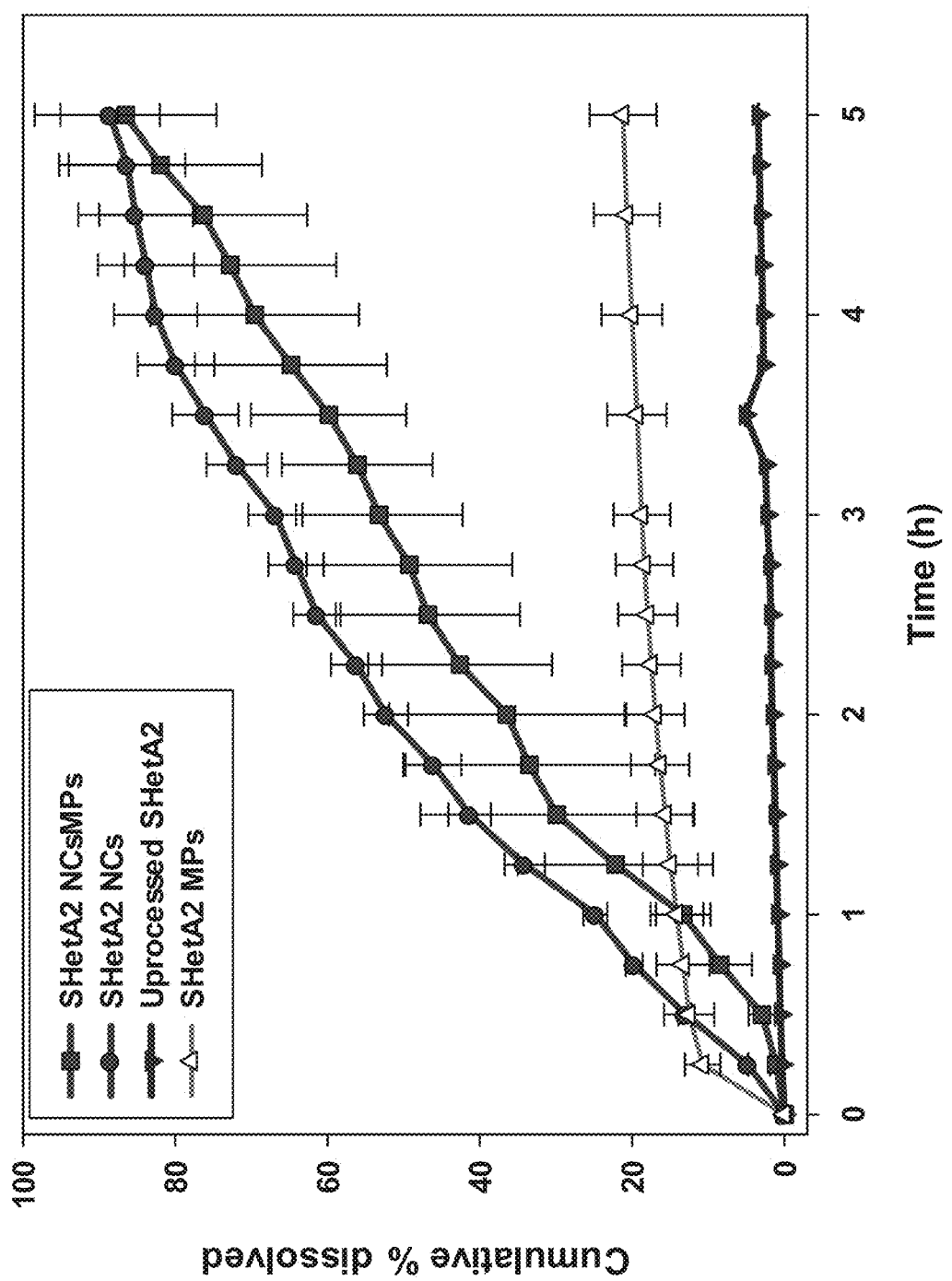

FIG. 9 shows dissolution profiles of SHetA2 NC-MPs, unprocessed SHetA2, and spray dried SHetA2 MPs of size range 2.82-4.46 µm. Cumulative percentage dissolved SHetA2 from unprocessed SHetA2, SHetA2 NCs, SHetA2 MPs, and SHetA2 NC-MPs.

DETAILED DESCRIPTION

The present disclosure, in at least certain non-limiting embodiments, is directed to the formation of drug microparticles by spray drying suspensions of drug nanocrystals suspended in a solvent, thereby reducing polydispersity and enabling customization of the size distribution and average size and volume of the microparticles so that specific lung regions (e.g., alveoli) can be targeted for improved therapy when the microparticles are administered, particularly as dry powder aerosols. Direct pulmonary administration of drugs formulated by the approach disclosed herein result in achieving drug concentrations in the lung that other routes of administration, such as oral or parenteral, cannot attain.

Before further describing various embodiments of the compounds, compositions, and methods of the present disclosure in more detail by way of exemplary description, examples, and results, it is to be understood that the compounds, compositions, and methods of the present disclosure are not limited in application to the details of specific embodiments and examples as set forth in the following description. The description provided herein is intended for purposes of illustration only and is not intended to be construed in a limiting sense. As such, the language used herein is intended to be given the broadest possible scope and meaning, and the embodiments and examples are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the present disclosure. However, it will be apparent to a person having ordinary skill in the art that the present disclosure may be practiced without these specific details. In other instances, features which are well known to persons of ordinary skill in the art have not been described in detail to avoid unnecessary complication of the description. It is intended that all alternatives, substitutions, modifications, and equivalents apparent to those having ordinary skill in the art are included within the scope of the present disclosure. Thus, while the compounds, compositions, and methods of the present disclosure have been described in terms of particular embodiments, it will be apparent to those of skill in the art that variations may be applied to the compounds, compositions, and/or methods and in the steps or in the sequence of steps of the methods described herein without departing from the concept, spirit, and scope of the inventive concepts described herein.

All patents, patent applications, and non-patent publications mentioned in the specification or referenced in any portion of this application are herein expressly incorporated by reference in their entirety to the same extent as if each individual patent, application, or publication was specifically and individually indicated to be incorporated by reference. Non-limiting examples thereof include U.S. Pat. Nos. 6,586,460; 7,612,107; 9,511,026; 9,750,696; and 9,795,562; and U.S. Provisional Patent Application No. 62/583,755.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, includes ranges of 1-20, 10-50, 50-100, 100-500, and 500-1,000, for example.

As used in this specification and claims, the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the terms "about" or "approximately" are used to indicate that a value includes the inherent variation of error for the composition, the method used to administer the composition, or the variation that exists among the study subjects. As used herein the qualifiers "about" or "approximately" are intended to include not only the exact value, amount, degree, orientation, or other qualified characteristic or value, but are intended to include some slight variations due to measuring error, manufacturing tolerances, observer error, wear and tear, and combinations thereof, for example. The terms "about" or "approximately," where used herein when referring to a measurable value such as an amount, a temporal duration, and the like, are meant to encompass, for example, variations of ±20%, or ±15%, or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 75% of the time, or at least 80% of the time, or at least 90% of the time, or at least 95% of the time, or at least 98% of the time.

As used herein, any reference to "one embodiment" or "an embodiment" means that a particular element, feature, structure, or characteristic described in connection with the embodiment is included in at least one embodiment and may be included in other embodiments. The appearances of the phrase "in one embodiment" in various places in the specification are not necessarily all referring to the same embodiment and are not necessarily limited to a single or particular embodiment. In addition, the use of the terms "one embodiment" and "an embodiment" are not to be construed as limiting in any matter of the scope of the present disclosure.

The term "pharmaceutically acceptable" refers to compounds and compositions which are suitable for administration to humans and/or animals without undue adverse side effects such as toxicity, irritation, and/or allergic response commensurate with a reasonable benefit/risk ratio. The compounds of the present disclosure may be combined with one or more pharmaceutically-acceptable excipients, including carriers, vehicles, diluents, and adjuvants which may improve solubility, deliverability, dispersion, stability, and/or conformational integrity of the compounds or conjugates thereof.

As used herein, the term "pure" or "substantially pure" means an object species is the predominant species present (i.e., on a molar basis it is more abundant than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure.

The terms "subject" and "patient" are used interchangeably herein and will be understood to refer an organism to which the compositions of the present disclosure are applied and used, such as (but not limited to) a vertebrate or more particularly to a warm blooded animal, such as (but not limited to) a mammal or bird. Non-limiting examples of animals within the scope and meaning of this term include dogs, cats, rats, mice, guinea pigs, chinchillas, horses, goats, cattle, sheep, zoo animals, Old and New World monkeys, non-human primates, and humans.

"Treatment" refers to therapeutic treatments. "Prevention" refers to prophylactic or preventative treatment measures or reducing the onset of a condition or disease. The term "treating" refers to administering the composition to a subject for therapeutic purposes and/or for prevention. Non-limiting examples of modes of administration include inhalation, oral, topical, retrobulbar, subconjunctival, transdermal, parenteral, subcutaneous, intranasal, intramuscular, intraperitoneal, intravitreal, and intravenous routes, including both local and systemic applications. In addition, the compositions of the present disclosure may be designed to provide delayed, controlled, extended, and/or sustained release using formulation techniques which are well known in the art.

The terms "therapeutic composition" and "pharmaceutical composition" refer to a composition comprising a poorly soluble drug that may be administered to a subject by any method known in the art or otherwise contemplated herein, wherein administration of the composition brings about a therapeutic effect as described elsewhere herein. In addition, the compositions of the present disclosure may be designed to provide delayed, controlled, extended, and/or sustained release using formulation techniques which are well known in the art.

The term "effective amount" refers to an amount of an active ingredient, such as a poorly soluble drug, which is sufficient to exhibit a detectable therapeutic or treatment effect in a subject without excessive adverse side effects (such as substantial toxicity, irritation, and allergic response) commensurate with a reasonable benefit/risk ratio when used in the manner of the present disclosure. The effective amount for a subject will depend upon the subject's type, size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

The term "ameliorate" means a detectable or measurable improvement in a subject's condition or symptom thereof. A detectable or measurable improvement includes a subjective or objective decrease, reduction, inhibition, suppression, limit, or control in the occurrence, frequency, severity, progression, or duration of the condition, or an improvement in a symptom or an underlying cause or a consequence of the condition, or a reversal of the condition. A successful treatment outcome can lead to a "therapeutic effect" or "benefit" of ameliorating, decreasing, reducing, inhibiting, suppressing, limiting, controlling, or preventing the occurrence, frequency, severity, progression, or duration of a condition, or consequences of the condition in a subject.

A decrease or reduction in worsening, such as stabilizing the condition, is also a successful treatment outcome. A therapeutic benefit therefore need not be complete ablation or reversal of the condition, or any one, most, or all adverse symptoms, complications, consequences, or underlying causes associated with the condition. Thus, a satisfactory endpoint may be achieved when there is an incremental improvement such as a partial decrease, reduction, inhibition, suppression, limit, control, or prevention in the occurrence, frequency, severity, progression, or duration, or inhibition or reversal of the condition (e.g., stabilizing), over a short or long duration of time (e.g., seconds, minutes, hours).

Where used herein, the term "poorly soluble drug" (a.k.a., "poorly water-soluble drug" and "low solubility drug") refers to a drug or bioactive agent which requires from 1000 to 10000 parts of solvent for 1 part of solute, and/or is a Class II (high permeability, low solubility) or Class IV (low permeability, low solubility) drug according to the Biopharmaceutics Classification System (BCS). Non-limiting examples of such poorly soluble drugs which may be used in the microparticulate compositions as disclosed or otherwise contemplated herein include, but are not limited to, those listed in U.S. Pat. Nos. 9,795,562; 9,750,696; and 9,511,026.

Where used herein in reference to a poorly soluble drug, the term "unprocessed" (e.g., "unprocessed drug") refers to a feedstock form of the poorly soluble drug which is initially provided before being processed into nanocrystals or nanocrystal microparticles as described in the present disclosure.

Where used herein in reference to a poorly soluble drug, the term "amorphous" (e.g., "amorphous drug") refers to a form of the poorly soluble drug which has a disordered arrangement of molecules and which does not possess a distinguishable crystal lattice, for example (but not by way of limitation), a drug which has been spray-dried according to methods of the present disclosure, without having first been converted into nanocrystals according to methods of the present disclosure.

Where used herein in reference to a compound, the term "apparent solubility" refers to the concentration (g/L) of the compound in a solvent at apparent equilibrium (i.e., supersaturation).

Currently, to the best of the inventors' knowledge, there is no available product of a drug in nanocrystal (NC) form as a powder. Also, there is currently no commercialized inhaled product for treatment of lung cancer or tuberculosis (TB). Additionally, there is no commercialized product comprising SHetA2 or other flexible heteroarotinoids. The compositions of the present disclosure differ from conventional technologies based on (for example, but not by way of limitation) fabrication method, route of delivery, form of the drug, microparticle size and size distribution, and/or lack of toxicity.

When NCs are combined with carrier materials to form microparticles (MPs) using the technology disclosed herein, the resulting nanocrystal microparticles (NC-MPs) can significantly increase the dissolution rate of the nanocrystalline drug (particularly of a poorly soluble drug) in the composition, by increasing their saturation solubility, which in turn increases drug absorption, resulting in high concentrations of the drug at the site of delivery. For example (but not by way of limitation), SHetA2 NC-MPs of the present disclosure significantly increase the dissolution rate of drugs by about 4-fold and about 25-fold when compared to amorphous SHetA2 MPs and unprocessed drug, respectively, and increased the saturation solubility by about 4.25-fold and about 15-fold when compared to amorphous SHetA2 MPs and unprocessed drug, respectively. Further, the use of an NC form of the drug increases the stability of the drug at the site of action and the shelf life of a product by decreasing the likelihood of degradation by the microenvironment or storage conditions, respectively.

The presently disclosed NC-MP drug formulations provide the capability of offering up to substantially 100% drug content at the site of action and enable the targeting of different regions of the respiratory tract and lung tissue. In addition, the microparticulate aggregation of the nanoparticles renders them more stable thermodynamically and prevents crystal growth in the microenvironment at the site of drug action.

Use of the presently disclosed NC-based dry powder aerosol formulations disclosed or otherwise contemplated herein to treat lung diseases allows for decreased dosage size while resulting in, for example (but not by way of limitation), faster dissolution, faster and enhanced absorption, and longer residence time, thereby increasing efficacy of treatment and decreasing side effects.

Certain non-limiting embodiments of the present disclosure are directed to microparticulate drug compositions that comprise microparticles that include NCs of a poorly soluble drug and a carrier (excipient) such as but not limited to mannitol, sorbitol, lactose, or microcrystalline cellulose.

The NCs may be provided with any size and/or shape that allows the microparticulate drug compositions formed therefrom to function in accordance with the present disclosure. For example, but not by way of limitation, the nanoparticles may have an average geometric diameter of less than about 2 μm, less than about 1.5 μm, less than about 1.0 μm, less than about 0.9 μm, less than about 0.8 μm, less than about 0.7 μm, less than about 0.6 μm, less than about 0.5 μm, less than about 0.4 μm, less than about 0.3 μm, less than about 0.2 μm, less than about 0.1 μm, less than about 0.09 μm, less than about 0.08 μm, less than about 0.07 μm, less than about 0.06 μm, less than about 0.05 μm, less than about 0.04 μm, less than about 0.03 μm, less than about 0.02 μm, less than about 0.01 μm, and the like. In addition, the average geometric diameter of the NCs may fall within a range of any two of the values listed above, such as (but not limited to), a range of from about 0.01 μm to about 1.0 μm, a range of from about 0.05 μm to about 0.5 μm, and the like.

The MPs comprising the NCs and the carrier material may be provided with any size that allows the microparticulate drug compositions to function in accordance with the present disclosure. For example, but not by way of limitation, the NC-MPs may an average geometric diameter of less than about 5 µm, less than about 4 µm, less than about 3.5 µm, less than about 3 µm, less than about 2.9 µm, less than about 2.8 µm, less than about 2.7 µm, less than about 2.6 µm, less than about 2.5 µm, less than about 2.4 µm, less than about 2.3 µm, less than about 2.2 µm, less than about 2.1 µm, less than about 2.0 µm, less than about 1.9 µm, less than about 1.8 µm, less than about 1.7 µm, less than about 1.6 µm, less than about 1.5 µm, less than about 1.4 µm, less than about 1.3 µm, less than about 1.2 µm, less than about 1.1 µm, less than about 1.0 µm, less than about 0.9 µm, less than about 0.8 µm, less than about 0.7 µm, less than about 0.6 µm, less than about 0.5 µm, less than about 0.4 µm, less than about 0.3 µm, less than about 0.2 µm, less than about 0.1 µm, and the like. In addition, the average geometric diameter of the NC-MPs may fall within a range of any two of the values listed above, such as (but not limited to), a range of from about 1.0 µm to about 3.5 µm, a range of from about 2.3 µm to about 2.9 µm, and the like.

In addition, the NC-MPs may have any shape that allows the microparticulate drug compositions to function as described herein. For example (but not by way of limitation), the NC-MPs may have an average volume diameter of less than about 10 µm, less than about 9 µm, less than about 8 µm, less than about 7 µm, less than about 6 µm, less than about 5 µm, less than about 4 µm, less than about 3.9 µm, less than about 3.8 µm, less than about 3.7 µm, less than about 3.6 µm, less than about 3.5 µm, less than about 3.4 µm, less than about 3.3 µm, less than about 3.2 µm, less than about 3.1 µm, less than about 3.0 µm, less than about 2.9 µm, less than about 2.8 µm, less than about 2.7 µm, less than about 2.6 µm, less than about 2.5 µm, less than about 2.4 µm, less than about 2.3 µm, less than about 2.2 µm, less than about 2.1 µm, less than about 2.0 µm, less than about 1.9 µm, less than about 1.8 µm, less than about 1.7 µm, less than about 1.6 µm, less than about 1.5 µm, less than about 1.4 µm, less than about 1.3 µm, less than about 1.2 µm, less than about 1.1 µm, less than about 1.0 µm, less than about 0.9 µm, less than about 0.8 µm, less than about 0.7 µm, less than about 0.6 µm, less than about 0.5 µm, less than about 0.4 µm, less than about 0.3 µm, less than about 0.2 µm, less than about 0.1 µm, and the like. In addition, the average volume diameter of the NC-MPs may fall within a range of any two of the values listed above, such as (but not limited to), a range of from about 3 µm to about 5 µm, a range of from about 5 µm to about 10 µm, and the like.

In one particular (but non-limiting) embodiment, the NCs have an average geometric diameter less than about 0.2 µm, and the NC-MPs have an average geometric diameter of less than about 2.7 µm and an average volume diameter of less than about 3.1 µm.

In certain non-limiting embodiments, the ratio of average volume diameter to average geometric diameter (i.e., $d_v/d_g$ ratio) of the NC-MPs of the present disclosure is in a range of from about 1 to about 10, such as (but not limited to), a range of from about 1 to about 9, a range of from about 1 to about 8, a range of from about 1 to about 7, a range of from about 1 to about 6, a range of from about 1 to about 5, a range of from about 1 to about 4, a range of from about 1 to about 3.5, a range of from about 1 to about 3, a range of from about 1 to about 2.5, a range of from about 1 to about 2, a range of from about 1.0 to about 1.5, and the like.

The active agent of the NC-MPs of the present disclosure may be any poorly soluble drug as defined or otherwise contemplated herein. One non-limiting class of poorly soluble drugs that may be utilized in accordance with the present disclosure are heteroarotinoids; non-limiting examples of heteroarotinoids that may be used as the active agent include (but are not limited to) any heteroarotinoid disclosed in U.S. Pat. No. 6,586,460 (see, for example, Columns 2-5 thereof) and U.S. Pat. No. 7,612,107 (see, for example, Columns 7-9 thereof). Particular non-limiting examples of heteroarotinoids that can be used as the active agent include SHetA2, SHetA3, SHetA4, SHetC2, SHet50, SHet65, SHet100, OHet72, NHet17, NHet86, and NHet90. In certain embodiments the active agent may be clofazimine nanocrystals.

The microparticulate drug compositions (i.e., NC-MPs) of the present disclosure may be formulated for administration via any mechanisms disclosed herein or otherwise contemplated by a person having ordinary skill in the art. In one non-limiting embodiment, the NC-MPs are formulated to be inhalable in a mammalian lung.

The microparticulate drug compositions of the present disclosure possess apparent solubilities, saturation solubilities, and/or dissolution rates that are increased over that of an unprocessed form of the drug. For example (but not by way of limitation), the apparent solubility, saturation solubility, and/or dissolution rate of the microparticulate drug composition may be increased when compared to the apparent solubility, saturation solubility, and/or dissolution rate of an unprocessed form of the poorly soluble drug by a factor of at least about 1.25-fold, at least about 1.5-fold, at least about 1.75-fold, at least about 2-fold, at least about 2.25-fold, at least about 2.5-fold, at least about 2.75-fold, at least about 3-fold, at least about 3.25-fold, at least about 3.5-fold, at least about 3.75-fold, at least about 4-fold, at least about 4.25-fold, at least about 4.5-fold, at least about 4.75-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, at least about 10-fold, at least about 11-fold, at least about 12-fold, and at least about 13-fold, at least about 14-fold, at least about 15-fold, at least about 16-fold, at least about 17-fold, at least about 18-fold, at least about 19-fold, at least about 20-fold, at least about 21-fold, at least about 22-fold, at least about 23-fold, at least about 24-fold, at least about 25-fold, at least about 26-fold, at least about 27-fold, at least about 28-fold, at least about 29-fold, at least about 30-fold, or higher. In addition, the apparent solubility, saturation solubility, and/or dissolution rate of the microparticulate drug composition may be increased by a factor that falls within a range of any two of the values listed above, such as (but not limited to), a range of from about 2-fold to about 5-fold, a range of from about 10-fold to about 25-fold, and the like.

Similarly, the microparticulate drug compositions of the present disclosure possess apparent solubilities, saturation solubilities, and dissolution rates that are increased over that of a microparticulate amorphous form of the poorly soluble drug. For example (but not by way of limitation), the apparent solubility, saturation solubility, and/or dissolution rate of the microparticulate drug composition may be increased when compared to the apparent solubility, saturation solubility, and/or dissolution rate of a microparticulate amorphous form of the poorly soluble drug by a factor of at least about 1.25-fold, at least about 1.5-fold, at least about 1.75-fold, at least about 2-fold, at least about 2.25-fold, at least about 2.5-fold, at least about 2.75-fold, at least about 3-fold, at least about 3.25-fold, at least about 3.5-fold, at least about 3.75-fold, at least about 4-fold, at least about 4.25-fold, at least about 4.5-fold, at least about 4.75-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, at least about 10-fold, at least about 11-fold, at least about 12-fold, and at least about 13-fold, at least about 14-fold, at least about 15-fold, at least about 16-fold, at least about 17-fold, at least about 18-fold, at least about 19-fold, at least about 20-fold, at least about 21-fold, at least about 22-fold, at least about 23-fold, at least about 24-fold, at least about 25-fold, at least about 26-fold, at least about 27-fold, at least about 28-fold, at least about 29-fold, at least about 30-fold, or higher. In addition, the apparent solubility, saturation solubility, and/or dissolution rate of the microparticulate drug composition may be increased by a factor that falls within a range of any two of the values listed above, such as (but not limited to), a range of from about 2-fold to about 5-fold, a range of from about 10-fold to about 25-fold, and the like.

In a particular (but non-limiting) embodiment, the microparticulate drug composition has an apparent solubility that is at least about 5-fold higher than that of an unprocessed form of the poorly soluble drug and at least about 2-fold higher than that of a microparticulate amorphous form of the poorly soluble drug.

Certain non-limiting embodiments of the present disclosure are also directed to a pharmaceutical composition comprising a dry powder aerosol formulation comprising any of the microparticulate drug compositions disclosed or otherwise contemplated herein.

Certain non-limiting embodiments of the present disclosure are also directed to a method of producing any of the microparticulate drug compositions or pharmaceutical compositions disclosed or otherwise contemplated herein. The method comprises at least the steps of: suspending NCs of a poorly soluble drug (as described herein above or otherwise contemplated herein) in a carrier solution to provide a nanocrystal/carrier suspension; and spray drying the nanocrystal/carrier suspension to form the inhalable microparticulate drug composition (as described herein above or otherwise contemplated herein). The carrier (also referred to herein as an excipient) may be, for example, a saccharide or saccharide derivative such as, but not limited to mannitol, sorbitol, lactose, or microcrystalline cellulose.

In a particular (but non-limiting) embodiment, the microparticulate drug compositions/pharmaceutical compositions of the present disclosure are produced using a bottom up method; thus, a micronization (milling) method is not used in their formation.

Certain non-limiting embodiments of the present disclosure are directed to a method that comprises administering to a subject in need thereof any of the pharmaceutical compositions disclosed or otherwise contemplated herein.

The pharmaceutical compositions may be administered via any mechanisms disclosed herein or otherwise contemplatable by a person having ordinary skill in the art. In one non-limiting embodiment, the administration occurs via an inhaler, which aerosolizes the NC-MPs.

The pharmaceutical compositions of the present disclosure may be administered for any purpose disclosed or otherwise contemplated herein, as well as for any purpose within the purview of a person having ordinary skill in the art. In one non-limiting embodiment, the pharmaceutical compositions are administered in a method of treating or reducing the occurrence of cancer. In another non-limiting embodiment, the pharmaceutical compositions are administered in a method of treating or reducing the occurrence of tuberculosis. However, these two treatment methods are not to be construed as limiting of the present disclosure, and any diseases, disorders, or conditions disclosed herein or otherwise contemplatable by a person having ordinary skill in the art (given the subject application) which may derive a therapeutic effect by treatment with the compositions disclosed herein also fall within the scope of the methods of the present disclosure.

In one particular (but non-limiting) embodiment, the microparticulate drug compositions or pharmaceutical compositions disclosed or otherwise contemplated herein comprise SHetA2, which induces apoptosis in cancer cells without harming normal cells.

Examples

The novel embodiments of the present disclosure, having now been generally described, will be more readily understood by reference to the following examples and embodiments, which are included merely for purposes of illustration of certain aspects and embodiments of the present disclosure, and are not intended to be limiting. The following detailed examples and embodiments are to be construed, as noted above, only as illustrative, and not as limitations of the present disclosure in any way whatsoever. Those skilled in the art will promptly recognize appropriate variations from the various compositions, structures, components, procedures, and methods.

Formation of SHetA2 Nanocrystals and Use in Production of Inhalable SHetA2 Microparticles Methods and Results:

Chemicals

Dichloromethane (DCM) (Sigma, St. Louis, Mo., USA), methanol (HPLC grade ≥99.9%, Sigma, St. Louis, Mo., USA), sodium acetate trihydrate (Reagent plus ≥99.0%, Sigma, St. Louis, Mo., USA), mannitol (≥98.0%, Sigma, St. Louis, Mo., USA), poly(vinyl alcohol) (PVA, $M_w$: 25000 Polysciences, Warrington, Pa., USA) and SHetA2.

Instruments

In this work, a sonic dismembrator (Fisher Scientific, Pittsburgh, Pa., USA) and an ultrasonic bath (Branson, Loveland, Colo., USA) were used to fabricate the drug nanocrystals (NCs). Buchi Mini Spray Dryer B-290 (New Castle, Del., USA) was used to manufacture the microparticles (MPs). The geometric diameter ($d_g$) of NCs and NC-MPs were measured directly from the images obtained with a scanning electron microscope (SEM) (JEOL JSM-880, JEOL USA, Inc., Peabody, Mass.) with the aid of ImageJ 1.49n software (NIH, USA). The morphology of the MPs was evaluated by SEM. The volume diameter ($d_v$) of NCs and MPs was measured by laser diffraction using a HELOS system with RODOS dry dispersing unit (Sympatec Inc., Lawrenceville, N.J.). The production and analysis of the products and compositions of the present disclosure are not limited to the use of these particular instruments. Any other instruments capable of functioning in a similar manner could be used in lieu of those described herein.

In Vivo

Friend Leukemia Virus B (FVB) male mice and Male Dunkin Hartley guinea pigs were used in in vivo experiments.

Fabrication of SHetA2 Nanocrystals

SHetA2 NCs were prepared using a bottom up approach. In one non-limiting embodiment, the process was formulated to yield NCs with the smallest possible geometric diameter ($d_g$) using Design of Experiments (DoE) software. Briefly, 75 mg of SHetA2 was dissolved in 1 mL of DCM. A round bottom flask containing 10 mL of 1% (w/v) PVA was placed in an ultrasonic bath. The SHetA2-DCM solution was injected into the PVA solution while operating simultaneously the sonic dismembrator and ultrasonic bath, each at different settings described below. The resulting NCs were then separated by centrifugation at 5500 rpm for 30 min. The pellet containing the NCs was washed with deionized water at least 3 times to remove residual PVA. The NCs in the washed pellet were then reconstituted in deionized water and stored at −80° C. The formulation and fabrication process was calculated to yield NCs with the smallest possible geometric diameter ($d_g$) using $2^4$ factorial design software (DESIGN-EXPERT® software; DoE, Minneapolis, Minn.)). The parameters entered in the DoE were drug concentration in the organic phase (30-75 mg/ml), sonication power (10-24 Watts), sonication time (30-60 minutes), and an ultrasonication time of 20-40 minutes, as shown in Table 1 below.

The value of $d_g$ calculated herein is an average of measurements of at least 200 individual NCs from each batch. The geometric standard deviation (GSD) of $d_g$ was calculated using equation I:

$$GSD = [D_{84\%}/D_{16\%}]^{1/2} \quad \text{(Equation I)}$$

where $D_{84\%}$ and $D_{16\%}$ represent the diameters at the cumulative percentile of 84% and 16% of the particle size distribution after it has been "normalized."

Spray Drying of SHetA2 NCs into MPs (SHetA2 NC-MPs)

The aerodynamic diameter ($d_a$) is the best parameter to use to predict how a particle or droplet will behave in an air stream. The $d_a$ is defined as the diameter of a unit density sphere that has the same terminal setting velocity in air as the actual particle and is described by equation II:

$$V_{TS} = r_0 D_a^2 g/18h = r_p D_v^2 g/18hc \quad \text{(Equation II)}$$

where $V_{TS}$ is the terminal settling velocity of the unit density sphere; $r_0$ is the unit density; g is the acceleration of gravity; h is the air viscosity; $r_p$ is the particle density; $D_v$ is the equivalent volume diameter; and c is the shape factor of the particle. This equation has important implications for the production of dry powder aerosols, as it implies that the terminal settling velocity of particles increases proportionately with their size. Thus, under the principles of lung deposition, large particles would be more likely to deposit by inertial impaction in the upper respiratory tract, where air velocity is high and the air flow is turbulent, whereas smaller particles would deposit by sedimentation in the terminal bronchioles and alveolar regions.

NCs from the batch of SHetA2 NCs with the smallest $d_g$ (experiment #11 from Table 1) were suspended with mannitol in water for formulation by spray-drying into inhalable nanocrystal microparticles (NC-MPs). The MP size ($d_g$ and $d_v$) and distribution GSD were optimized by entering the following formulation composition and manufacturing parameters into a second DoE: feed concentration (0.5% to 1.5% of NCs), spray drying temperature (120° C. to 150° C.), and mannitol ratio (10% to 50%). For example, the feed concentration represents the grams (g) of total solids (NCs and mannitol) suspended in milliliters (mL) of deionized water. Thus, a feed concentration of 0.5% represents 0.005 g of total solids per 1.0 mL of water. In one example, 50 mg of total solids suspended in 1 mL of deionized water results in a 0.5% feed concentration. An "X %" mannitol ratio indicates that X % of the total solids was mannitol, and (100−X) % of the total solids was NCs. For example, the feed concentration for #8 in Table 2 is 0.5%, which means 50 mg of total solids (NCs and mannitol) was suspended in 10 mL of deionized water. The mannitol ratio was 50%, indicating that 50% of the total solids was mannitol, and 50% of the total solids was NCs. Thus, in the case of experiment #8 in Table 2, 25 mg of NCs and 25 mg of mannitol were suspended in 10 mL of water, providing a 0.5% feed concentration and a 50% mannitol ratio. SEM images of SHetA2 NCs and NC-MPs are shown in Panels (a) and (b) of FIG. 1, respectively. Composition results are shown in Table 2.

TABLE 1

Experimental Parameters and Sizes and Size Distributions of SHetA2 NCs

| Exp. # | Sonication Power (W) | Sonication Time (min) | Drug conc. (mg/mL) | Ultrasonication Time (min) | $d_g$ (μm) | GSD | Span |
|---|---|---|---|---|---|---|---|
| 1 | 10 | 30 | 30 | 20 | 0.396 | 1.85 | 0.0-1.40 |
| 2 | 24 | 30 | 30 | 20 | 0.573 | 1.87 | 0.0-1.00 |
| 3 | 10 | 60 | 30 | 20 | 0.388 | 1.75 | 0.0-0.80 |
| 4 | 24 | 60 | 30 | 20 | 0.380 | 1.69 | 0.0-0.80 |
| 5 | 10 | 30 | 30 | 40 | 0.372 | 1.76 | 0.0-0.70 |
| 6 | 24 | 30 | 30 | 40 | 0.343 | 1.57 | 0.0-0.60 |
| 7 | 10 | 60 | 30 | 40 | 0.357 | 1.71 | 0.0-0.80 |
| 8 | 24 | 60 | 30 | 40 | 0.421 | 1.71 | 0.0-1.00 |
| 9 | 10 | 30 | 75 | 20 | 0.710 | 1.58 | 0.0-0.70 |
| 10 | 24 | 30 | 75 | 20 | 0.690 | 1.70 | 0.0-0.35 |
| 11 | 10 | 60 | 75 | 20 | 0.157 | 2.00 | 0.0-1.00 |
| 12 | 24 | 60 | 75 | 20 | 0.635 | 1.60 | 0.0-1.30 |
| 13 | 10 | 30 | 75 | 40 | 0.602 | 1.58 | 0.0-0.80 |
| 14 | 24 | 30 | 75 | 40 | 0.477 | 1.63 | 0.0-1.00 |
| 15 | 10 | 60 | 75 | 40 | 0.439 | 1.61 | 0.0-1.20 |
| 16 | 24 | 60 | 75 | 40 | 0.557 | 1.54 | 0.0-1.40 |

TABLE 2

Spray Drying Parameters and Sizes and Size Distributions of SHetA2 NC-MPs

| Exp. # | Feed Conc. % | Mannitol Ratio % | Temperature (° C.) | $d_v$ | GDS ($d_v$) | $d_g$ | GSD ($d_g$) | Yield % |
|---|---|---|---|---|---|---|---|---|
| 1 | 1.5 | 10 | 150 | 3.45 | 1.68 | 1.87 | 1.32 | 37.80 |
| 2 | 0.5 | 10 | 120 | 2.99 | 1.60 | 2.62 | 1.22 | 20.72 |
| 3 | 0.5 | 10 | 150 | 3.04 | 1.62 | 2.60 | 1.33 | 17.52 |
| 4 | 1.5 | 50 | 120 | 2.62 | 1.68 | 1.81 | 1.35 | 36.81 |
| 5 | 1.5 | 10 | 120 | 3.08 | 1.59 | 2.57 | 1.28 | 14.94 |
| 6 | 1.5 | 50 | 150 | 2.69 | 3.30 | 2.22 | 1.33 | 35.00 |
| 7 | 0.5 | 50 | 150 | 2.41 | 1.70 | 1.53 | 1.19 | 20.90 |
| 8 | 0.5 | 50 | 120 | 2.53 | 1.70 | 2.30 | 1.36 | 35.00 |

Particle Size Distribution of NCs and NC-MPs

The value of $d_g$ is an average of measurements of at least 200 individual NCs from each batch. The morphology of the MPs was evaluated by SEM. The value of $d_v$ is an average of measurements of at least 200 individual MPs from each batch. Measurements were performed in triplicate at a dispersion pressure of 0.5 bars. The geometric standard deviation (GSD) of both $d_g$ and $d_v$ was calculated using equation I.

Figure 1:
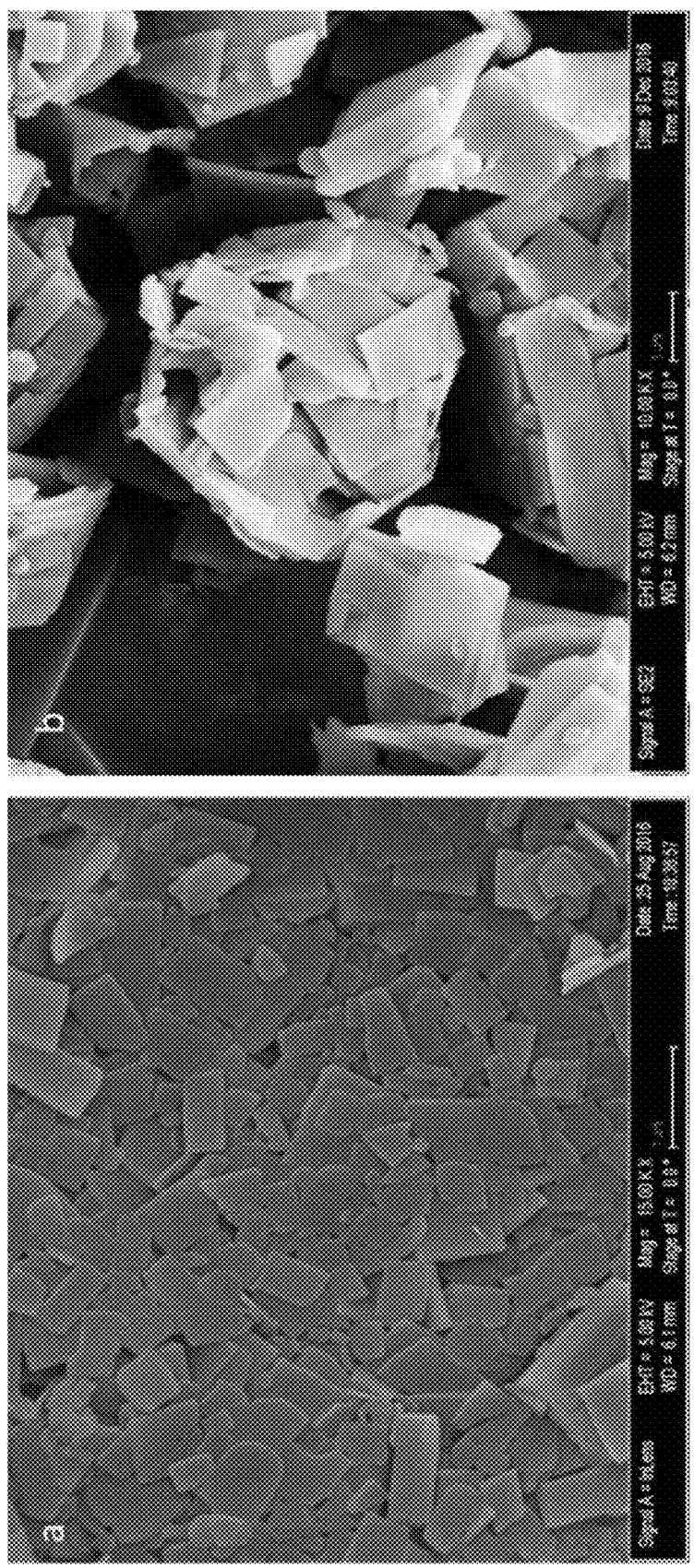
Figure 2:
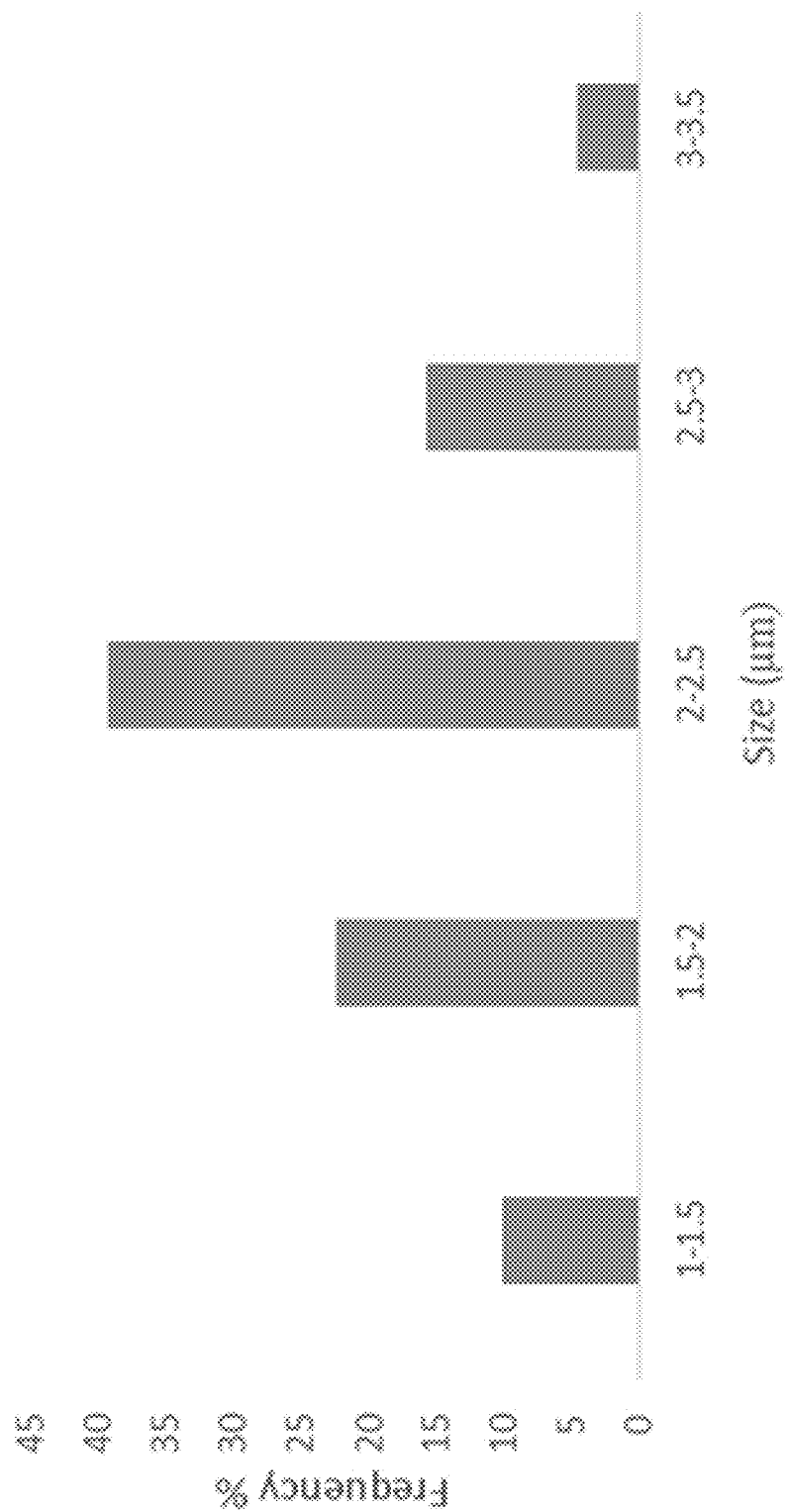

The size of NC-MPs produced ranged from $d_v$=3.45 μm and GSD=3.30 to $d_v$=2.41 μm and GSD=1.59. The MPs of experiment #8 (Table 2) provided a favorable yet non-limiting embodiment of an inhalable formulation; the composition comprised MPs having an average volume diameter, $d_v$=2.53 μm±0.08. As shown in FIG. 2, 95% of the microparticles in this batch had particles sizes in an alveolar-respirable size range (1 μm to 3.5 μm). In non-limiting embodiments, Panel (b) of FIG. 1 shows the morphology of MPs produced from the spray dried NCs (i.e., NC-MPs). In certain non-limiting embodiments, the NC-MPs of the present disclosure may be produced using a nanocrystal-mannitol suspension comprising a feed concentration in a range of from about 0.45% to about 0.75% nanocrystals, a mannitol ratio in a range of from about 30% to about 50%, and a spray drying temperature in a range of from about 100° C. to about 120° C.

In certain embodiments, the NC-MPs of the compositions have a sufficiently small average size (diameter $d_v$) distribution (e.g., 95% of particles) that they can enter alveoli, which have openings with an average size of approximately 3 μm or less. In certain embodiments, the NC-MPs are sized to be able to enter bronchioles, i.e., have sizes at least in the range of from about 3 μm to about 5 μm, or less. In certain embodiments, the NC-MPs are sized to be able to enter the trachea, i.e., have sizes at least in the range of from about 5 μm to about 10 μm, or less. The term $d_g$ refers to geometric diameter. The term $d_v$ refers to volume diameter. The term $d_a$ refers to aerodynamic diameter. In certain non-limiting embodiments, the $d_v/d_g$ ratio of the NC-MP compositions of the present disclosure is in a range of from about 1.0 to about 1.5. In certain non-limiting embodiments, the $d_v/d_g$ ratio of the NC-MP compositions of the present disclosure is in a range of from about 1 to about 3.

In Vitro Aerosol Performance of SHetA2 NC-MPs

The Next Generation Impactor (NGI) was employed in order to quantify in vitro lung deposition of SHetA2 NC-MPs. The NGI consists of eight collection cups corresponding to seven size fractionation stages of each of the regions of the respiratory tract. The deposition pattern of SHetA2 on the stages of NGI after aerosolization of SHetA2 NC-MPs powder using SPIRIVA® HANDIHALER® (tiotropium bromide inhalation powder; Boehringer Ingelheim Pharmaceuticals, Inc., Ridgefield, Conn.) is shown in FIG. 7. The amount of the emitted (delivered dose) drug recovered from the induction port (which mimics the human throat) was around 10.4%. Approximately 35% of the SHetA2 NC-MPs were larger than 8.06 μm, 18% were between 8.06 and 4.46 μm, and 18% were between 4.46 and 2.82 μm. The mass median aerodynamic diameter (MMAD) of the SHetA2 NC-MPs was found to be 3.24±0.15 μm with a GSD=1.6±0.2 (MMAD is defined as the diameter at which 50% of the particles by mass are larger and 50% are smaller). The emitted dose (ED) % and fine particle fraction (FPF$_{4.46}$) (%) were determined as 67.89±1.02 and 36.77±2.57, respectively. The FPF is the fraction of particles emitted by the device that would be deposited in the alveolar region of the lung (0.34-4.46 μm).

Apparent Maximum Solubility of SHetA2 NCs and SHetA2 NC-MPs

The apparent maximum solubility profiles of SHetA2 NCs, SHetA2 NC-MPs, unprocessed SHetA2 (i.e., unprocessed drug), and spray dried SHetA2 MPs (i.e., microparticulate amorphous drug) are shown in FIG. 8. The highest drug solubility was achieved at first 5 min by SHetA2 NC-MPs (7.14±0.84 μg/mL) followed by SHetA2 NCs (6.42±0.32 μg/mL), spray dried SHetA2 MPs (1.68±0.16 μg/mL), and unprocessed SHetA2 (0.48±0.11 μg/mL). Even though the spray dried SHetA2 MPs had amorphous structure, SHetA2 NC-MPs and SHetA2 NCs showed 4.24- and 3.82-fold higher apparent solubility, respectively (FIG. 8). SHetA2 NC-MPs and spray dried SHetA2 MPs followed a similar dissolution profile after 45 min. On the contrary, SHetA2 NCs showed a higher dissolution profile with a fluctuated pattern for the first 6 h due to growth of the NCs into bigger particles. At 45 min, the concentration of SHetA2 was 2.82±1.36 μg/mL; at 2 h, the SHetA2 concentration was 4.49±1.02 μg/mL; and in the 3-6 h period, the SHetA2 concentration decreased from 1.67 μg/mL to 1.19 μg/mL, respectively. After 6 h, SHetA2 NCs followed a similar dissolution profile with the other two formulations.

Dissolution Profile of SHetA2 NC-MPs, Unprocessed SHetA2, and Spray Dried SHetA2 MPs of Size Range 2.82-4.46 μm The mean cumulative percentage of SHetA2 dissolved versus time data for SHetA2 NCs, SHetA2 NC-MPs, spray dried SHetA2 MPs, and unprocessed SHetA2 is shown in FIG. 9. MPs in sizes 2.82-4.46 μm were studied, because the particles in this size range are deposited in the alveolar region of the lungs. The cumulative percentage of SHetA2 dissolved for SHetA2 NCs and SHetA2 NC-MPs are significantly high compared to spray dried SHetA2 MPs and unprocessed SHetA2. The concentration of SHetA2 increased at a constant rate for SHetA2 NCs and SHetA2 NC-MPs until 5 h. The cumulative percentage of SHetA2 dissolved from SHetA2 NCs and SHetA2 NC-MPs reached 86.55±8.9% and 88.56±6.52%, respectively. In the case of spray dried SHetA2 MPs, there was a prompt release within the first 15 min, then SHetA2 concentration increased slowly until leveling at a cumulative percentage of 21.19±4.40%. In contrast, the unprocessed SHetA2 dissolved only 3.51±0.9%.

In Vivo Experiments

In vivo experiments were carried out to characterize the disposition (absorption, distribution, and elimination) of SHetA2 after pulmonary administration of SHetA2 NC-MPs and to make a comparison to that after pulmonary administration of SHetA2 MPs produced by spray-drying and oral administration of SHetA2 NCs.

MPs formed with SHetA2 NCs (NC-MPs) were administered to mice by the pulmonary routes (12.5 mg/kg and 25 mg/kg) and by oral routes and compared to the administration of 10 mg/kg of a SHetA2 suspension solution (4 mg/mL unprocessed SHetA2 in 0.2% of kolliphor). SHetA2 concentrations were determined in bronchio-alveolar lavage (BAL) and lung tissue at different time points.

Figure 3:
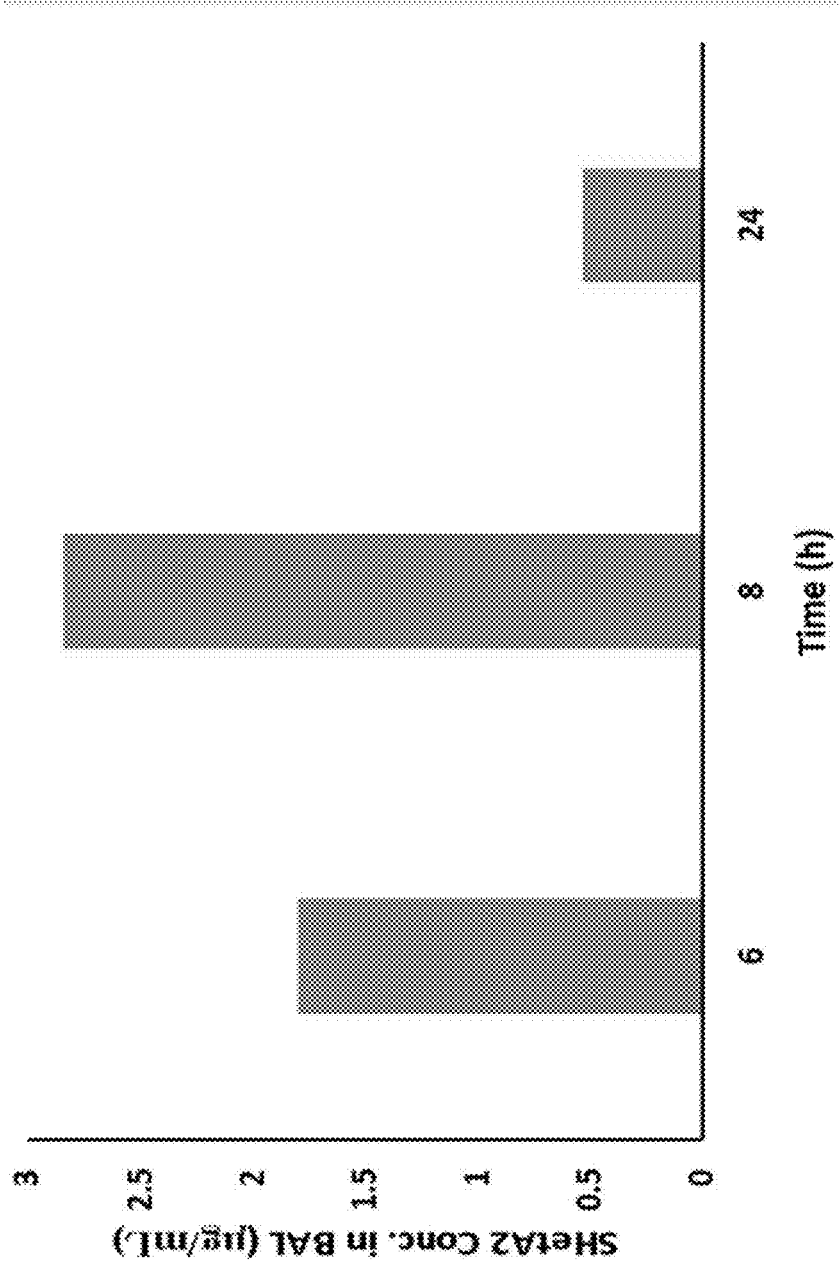
FIG. 3 shows concentration of SHetA2 in guinea pig BAL samples after administration of a 10 mg/kg dose of a SHetA2 suspension solution.

SHetA2 was detected in the BAL of animals dosed with 10 mg/kg of the SHetA2 suspension solution at 6, 8, and 24 hours post-administration, indicating that there was drug remaining to be absorbed from the airways into the lung tissue of these animals (FIG. 3). In contrast, no SHetA2 could be detected in the BAL of animals dosed with the NC-MPs at any time point, indicating that SHetA2 nanocrystals delivered as NC-MPs were dissolved and absorbed immediately upon delivery.

Figure 4:
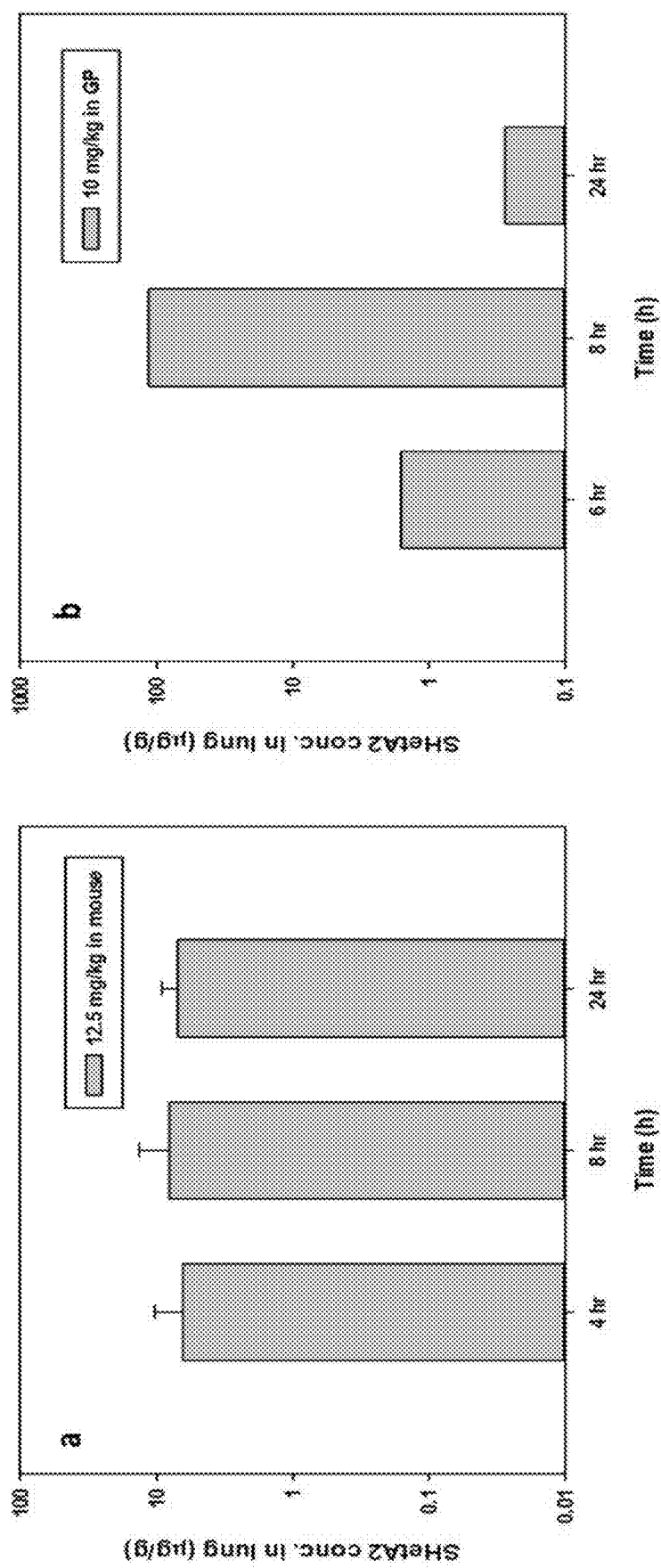
FIG. 4 shows a time-course distribution of SHetA2 concentrations in lung tissue after administration of (a) SHetA2 as NC-MPs and (b) a SHetA2 suspension solution.

Moreover, as shown in FIG. 4, while the SHetA2 concentrations in lung tissue were sustained and constant in lung tissue after pulmonary administration of SHetA2 NC-MPs (Panel (a) of FIG. 4), SHetA2 concentrations were variable after pulmonary administration of the SHetA2 suspension solution (Panel (b) of FIG. 4). This has important implications for the treatment of lung diseases, since SHetA2 delivery via NC-MPs results in lung concentrations which remain above therapeutic levels for the treatment of TB and cancer, while they are below therapeutic levels for TB treatment for a significant time period when SHetA2 is administered as the suspension solution. These results demonstrate that NC-MPs are more rapidly dissolved and absorbed into the lung tissue compared to SHetA2 administered as the suspension solution.

Figure 5:
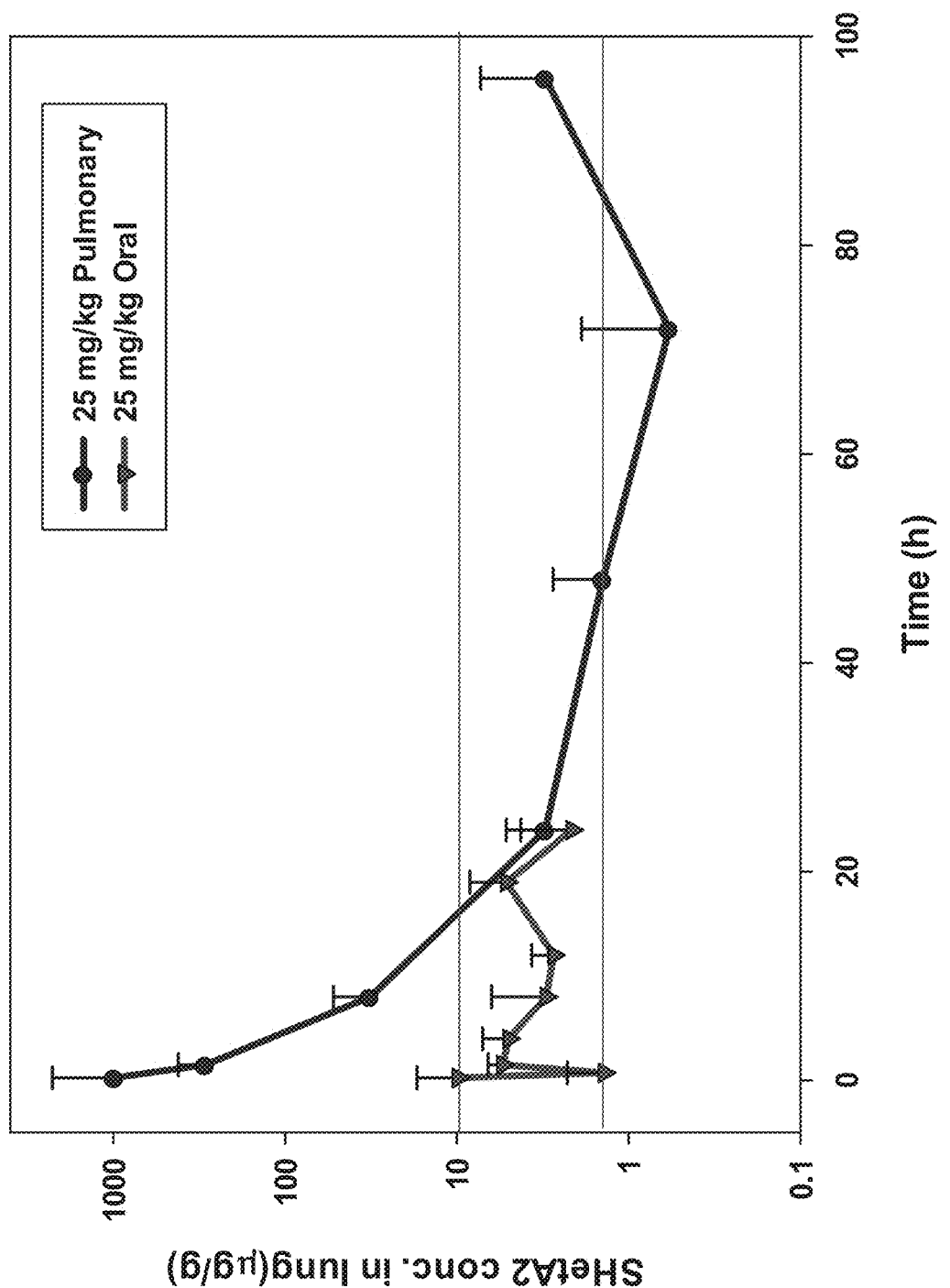
FIG. 5 shows SHetA2 concentrations in lung tissue after administration of NC-MPs via pulmonary and oral routes.

The comparison between lung tissue concentrations of SHetA2 NC-MPs after oral administration vs. pulmonary administration was studied, and the results are shown in FIG. 5. Lower concentrations of SHetA2 were observed at all times in the oral group compared to that after the pulmonary group (insufflation group). Moreover, drug concentrations were sustained after pulmonary administration and were detectable for a 4-fold longer duration compared to those after oral administration, demonstrating the superiority of delivering the NC-MP formulation via the pulmonary route. Pharmacokinetic parameters of the NC-MPs delivered via pulmonary vs. oral routes, including the area under the curve (AUC), apparent total body clearance (CL), elimination rate constant (K), half-life ($t_{1/2}$), and relative bioavailability were obtained by analyzing lung drug concentration measurements using PHOENIX® WINNONLIN® software (Certara, L.P., Princeton, N.J.). Results are shown in Table 3.

was cleared significantly faster from the lungs after oral administration compared to pulmonary administration, which is also evidenced by the 10-fold longer half-life when the drug is administered by the pulmonary route. Therefore, the apparent bioavailability of the drug is 30-fold larger after pulmonary administration using the oral route as reference. This demonstrates that pulmonary (versus oral) administration of NC-MPs significantly increased the bioavailability of SHetA2, and thus would also increase the bioavailability of other poorly soluble compounds.

Figure 6:
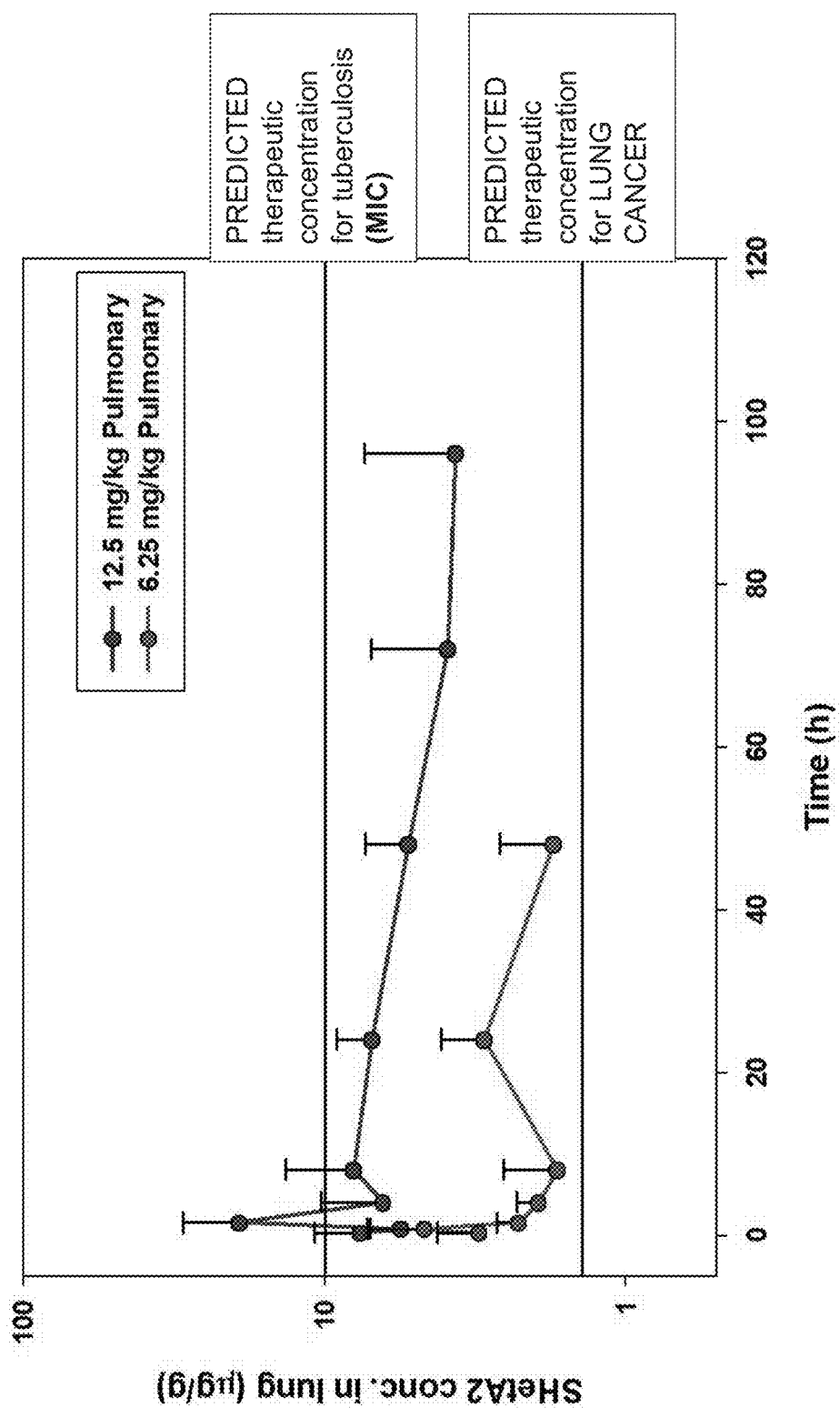
FIG. 6 shows SHetA2 lung concentration profiles in lungs over time for 12.5 mg/kg and 6.25 mg/kg doses after pulmonary administration.

Results from an experiment comparing drug concentration over time versus dosage (25 mg/kg and 12.5 mg/kg) with pulmonary administration of SHetA2 NC-MPs are shown in FIG. 6. Similar SHetA2 lung concentration profiles were observed between the two different doses, though the absolute concentration was greater for the higher dosage.

Pharmacokinetic parameters, including the AUC, apparent total body clearance (CL), elimination rate constant (K), half-life (t½), and relative bioavailability, were analyzed by PHOENIX® WINNONLIN® software (Certara, L.P., Princeton, N.J.). As expected, pulmonary administration exhibited significantly larger AUC compared to the oral route. Also, there is a significant difference between CL of oral and pulmonary routes as a result of deposition of SHetA2 in the lungs. Regarding the half-lives of the two different routes, the difference is significantly large, again due to disposition of SHetA2 in the lungs.

Quantitative descriptors of particle size are the projected area diameter, better known as geometric diameter ($d_g$) and its equivalent volume diameter ($d_v$). The $d_g$ of a particle is obtained from two-dimensional images generated by microscopy and represents the diameter of a circular disc with the same projected area as the particle being examined. The $d_v$ is the diameter of a sphere of the same volume to the particle, which is usually determined by laser diffraction or light obscuration methods. Each of these descriptors has limitations, as $d_g$ cannot discriminate the existence of powder aggregates, and as $d_v$ gives no information about primary particle size and morphology. Thus, both descriptors are usually determined for inhalable dry powders, and their difference in magnitude is used to predict if the powder is aggregated, and in some cases, the extent of aggregation. Still, these two dimensions have limited application to particles deposited in the respiratory tract, as they do not account for the density of the particle with respect to its mass, its shape, or their influence when the powder is dispersed in an air stream.

It should be noted that SHetA2 is provided only as one example of a drug that may be utilized in accordance with the present disclosure. The active agent of the microparticulate drug compositions (NC-MPs) of the present disclosure is not intended to be limited to SHetA2; rather, the scope of

TABLE 3

Pharmacokinetic parameters of the NC-MPs delivered via pulmonary vs. oral routes

| Treatment Route (dose) | AUC∞ (μg · h/mL) | AUC dose (μg · h/mL) | CL (L/h · kg) | V (L/kg) | λ ($h^{-1}$) | $t_{1/2}$ (h) | MRT (h) | Cmax (μg/mL) | Tmax (h) |
|---|---|---|---|---|---|---|---|---|---|
| Oral 25 mg/kg | 6.17 | 3.80 | 101.24 | 1123.19 | 0.09 | 7.69 | 12.07 | 0.76 | 0.25 |
| Insufflation 12.5 mg/kg | 92.90 | 55.44 | 6.73 | 752.43 | 0.01 | 77.52 | 104.06 | 7.15 | 0.25 |

The AUC after pulmonary administration was significantly larger than that after oral administration. The drug the present disclosure includes the use of any poorly soluble drug as defined or otherwise contemplated herein. In particular, other heteroarotinoids that may be used as the active agent include (but are not limited to) any heteroarotinoid disclosed in U.S. Pat. No. 6,586,460 (see, for example, Columns 2-5 thereof) and U.S. Pat. No. 7,612,107 (see, for example, Columns 7-9 thereof); non-limiting examples thereof include SHetA2, SHetA3, SHetA4, SHetC2, SHet50, SHet65, SHet100, OHet72, NHet17, NHet86, and NHet90.

In at least certain non-limiting embodiments, the present disclosure is directed to a microparticulate drug composition, comprising microparticles comprising a carrier and nanocrystals of a poorly soluble drug, wherein the nanocrystals have an average geometric diameter of less than about 0.2 µm; and wherein the microparticles have an average geometric diameter of less than about 2.7 µm and an average volume diameter of less than about 3.1 µm. The microparticles of the microparticulate drug composition may comprise a ratio of the average volume diameter to the average geometric diameter in a range of from about 1 to about 3. The poorly soluble drug may comprise a heteroarotinoid. The heteroarotinoid may be selected from the group consisting of SHetA2, SHetA3, SHetA4, SHetC2, SHet50, SHet65, SHet100, OHet72, NHet17, NHet86, and NHet90. The microparticles may be sized to be inhalable in a mammalian lung. The microparticulate drug composition may have an apparent solubility that is at least about 5-fold higher than that of an unprocessed form of the poorly soluble drug and at least about 2-fold higher than that of a microparticulate amorphous form of the poorly soluble drug.

In other non-limiting embodiments, the present disclosure is directed to a pharmaceutical composition, comprising a dry powder aerosol formulation comprising a microparticulate drug composition, wherein the microparticulate drug composition comprises microparticles comprising a carrier and nanocrystals of a poorly soluble drug, wherein the nanocrystals have an average geometric diameter of less than about 0.2 µm, and wherein the microparticles have an average geometric diameter of less than about 2.7 µm and an average volume diameter of less than about 3.1 µm. The microparticles of the microparticulate drug composition of the pharmaceutical composition may comprise a ratio of the average volume diameter to the average geometric diameter in a range of from about 1 to about 3. The microparticulate drug composition of the pharmaceutical composition may have an apparent solubility that is at least about 5-fold higher than that of an unprocessed form of the poorly soluble drug and at least about 2-fold higher than that of a microparticulate amorphous form of the poorly soluble drug. The poorly soluble drug may comprise a heteroarotinoid. The heteroarotinoid may be selected from the group consisting of SHetA2, SHetA3, SHetA4, SHetC2, SHet50, SHet65, SHet100, OHet72, NHet17, NHet86, and NHet90. The poorly soluble drug may be clofazimine. The microparticles of the pharmaceutical composition may be sized to be inhalable in a mammalian lung.

In other non-limiting embodiments, the present disclosure is directed to a method of producing a pharmaceutical composition comprising a dry powder aerosol formulation of a microparticulate drug composition, the method comprising the steps of suspending nanocrystals of a poorly soluble drug with a carrier solution (e.g., mannitol, lactose, sorbitol, microcrystalline cellulose) to provide a nanocrystal/carrier suspension, wherein the nanocrystals have an average geometric diameter of less than about 0.2 µm; and spray drying the nanocrystal/carrier suspension to form an inhalable microparticulate drug composition, wherein the microparticulate drug composition comprises microparticles comprising nanocrystals of the poorly soluble drug dispersed in the carrier, wherein the microparticles have an average geometric diameter of less than about 2.7 µm and an average volume diameter of less than about 3.1 µm. The microparticles of the microparticulate drug composition used in the method may comprise a ratio of the average volume diameter to the average geometric diameter in a range of from about 1 to about 3. The microparticulate drug composition may have an apparent solubility that is at least about 5-fold higher than that of an unprocessed form of the poorly soluble drug and at least about 2-fold higher than that of a microparticulate amorphous form of the poorly soluble drug. The poorly soluble drug may comprise a heteroarotinoid. The heteroarotinoid may be selected from the group consisting of SHetA2, SHetA3, SHetA4, SHetC2, SHet50, SHet65, SHet100, OHet72, NHet17, NHet86, and NHet90. The microparticles may be sized to be inhalable in a mammalian lung.

In other non-limiting embodiments, the present disclosure is directed to a method, comprising the step of administering to a subject in need thereof a pharmaceutical composition comprising a dry powder aerosol formulation of a microparticulate drug composition, wherein the microparticulate drug composition comprises microparticles comprising a carrier and nanocrystals of a poorly soluble drug, wherein the nanocrystals have an average geometric diameter of less than about 0.2 µm, and wherein the microparticles have an average geometric diameter of less than about 2.7 µm and an average volume diameter of less than about 3.1 µm. The microparticles of the microparticulate drug composition used in the method may comprise a ratio of the average volume diameter to the average geometric diameter in a range of from about 1 to about 3. The microparticulate drug composition may have an apparent solubility that is at least about 5-fold higher than that of an unprocessed form of the poorly soluble drug and at least about 2-fold higher than that of a microparticulate amorphous form of the poorly soluble drug. The poorly soluble drug may comprise a heteroarotinoid. The heteroarotinoid may be selected from the group consisting of SHetA2, SHetA3, SHetA4, SHetC2, SHet50, SHet65, SHet100, OHet72, NHet17, NHet86, and NHet90. The pharmaceutical composition may be administered using an inhaler. The method may be a method of treating or reducing the occurrence of cancer or tuberculosis. The carrier (excipient) may be, for example, a saccharide or saccharide derivative such as, but not limited to mannitol, sorbitol, lactose, or microcrystalline cellulose.

While the present disclosure has been described herein in connection with certain embodiments so that aspects thereof may be more fully understood and appreciated, it is not intended that the present disclosure be limited to these particular embodiments. On the contrary, it is intended that all alternatives, modifications, and equivalents are included within the scope of the present disclosure as defined herein. Thus the examples described above, which include particular embodiments, will serve to illustrate the practice of the present disclosure, it being understood that the particulars shown are by way of example and for purposes of illustrative discussion of particular embodiments only and are presented in the cause of providing what is believed to be the most useful and readily understood description of procedures as well as of the principles and conceptual aspects of the present disclosure.

Changes may be made in the formulation of the various compositions described herein, the methods described herein, or in the steps or the sequence of steps of the methods described herein without departing from the spirit and scope of the present disclosure. Further, while various embodiments of the present disclosure have been described in claims herein below, it is not intended that the present disclosure be limited to these particular claims. Applicant reserves the right to amend, add to, or replace the claims indicated herein below in subsequent patent applications.

What is claimed is:

1. A method of producing a pharmaceutical composition comprising a dry powder aerosol formulation of a microparticulate drug composition, the method comprising the steps of:
    producing a batch of nanocrystals consisting of a poorly soluble drug, wherein the nanocrystals are produced by (1) providing the poorly soluble drug in an organic solvent at a drug concentration in a range of from about 30 mg/ml to about 75 mg/ml to form a mixture, sonicating the mixture for a time in a range of from about 30 minutes to about 60 minutes, and (3) ultrasonicating the mixture for a time in a range of from about 20 minutes to about 40 minutes, wherein the poorly soluble drug is a heteroarotinoid wherein the nanocrystals thereby formed have an average geometric diameter of less than about 0.2 µm, and wherein a micronization method is not used in the production of the nanocrystals;
    dispersing the batch of nanocrystals into a carrier solution, forming a nanocrystal/carrier suspension comprising a feed concentration in a range of from about 0.45% to about 0.75% nanocrystals, and a carrier ratio in a range of from about 30% to about 50%; and
    spray drying the nanocrystal/carrier suspension at a spray drying temperature in a range of from about 100° C. to about 120° C. to form a microparticulate drug composition, wherein the microparticulate drug composition comprises microparticles comprising the nanocrystals dispersed in the carrier, wherein the microparticles have an average geometric diameter of less than about 2.7 µm and an average volume diameter of less than about 3.1 µm, and wherein the microparticles have a dissolution rate that is at least about 5-fold higher than that of an unprocessed form of the poorly soluble drug and at least about 2-fold higher than that of microparticles comprising an amorphous form of the poorly soluble drug, that consist of the poorly soluble drug.

2. The method of claim 1, wherein the carrier is selected from the group consisting of mannitol, sorbitol, lactose, and microcrystalline cellulose.

3. The method of claim 1, wherein the microparticles comprise a ratio of the average volume diameter to the average geometric diameter in a range of from about 1 to about 3.

4. The method of claim 1, wherein the heteroarotinoid is selected from the group consisting of SHetA2, SHetA3, SHetA4, SHetC2, SHet50, SHet65, SHet100, OHet72, NHet17, NHet86, and NHet90.

5. The method of claim 1, wherein the microparticles are sized to be inhalable in a mammalian lung.

6. The method of claim 1, wherein in (1) of the step of producing the batch of nanocrystals, the mixture is sonicated at a sonication power in a range of from about 10 Watts to about 24 Watts.

* * * * *

UNITED STATES PATENT AND TRADEMARK OFFICE
CERTIFICATE OF CORRECTION

PATENT NO. : 11,534,397 B2
APPLICATION NO. : 17/171151
DATED : December 27, 2022
INVENTOR(S) : Lucila Garcia-Contreras, Sevim Manolya Hatipoglu and Doris Mangiaracina Benbrook It is certified that error appears in the above-identified patent and that said Letters Patent is hereby corrected as shown below:

On the Title Page

Under (72) Inventors: Delete "Manglaracina" and replace with -- Mangiaracina --

Signed and Sealed this
Seventh Day of February, 2023

Katherine Kelly Vidal
*Director of the United States Patent and Trademark Office*